United States Patent [19]

Debernardis et al.

[11] Patent Number: 4,473,586

[45] Date of Patent: Sep. 25, 1984

[54] AMINOALKYL DIHYDRONAPHTHALENES

[75] Inventors: John F. Debernardis, Lake Villa; David L. Arendsen, Libertyville; Martin Winn, Deerfield, all of Ill.

[73] Assignee: Abbott Laboratories, North Chicago, Ill.

[21] Appl. No.: 374,352

[22] Filed: May 3, 1982

[51] Int. Cl.³ .................. A61K 31/18; A61K 31/165; A61K 31/135; C07C 143/72
[52] U.S. Cl. .................... 424/321; 564/99; 564/219; 564/220; 564/222; 564/307; 564/336; 424/324; 424/330
[58] Field of Search ............. 564/336, 222, 99, 219, 564/220, 307; 424/320, 321, 330, 324

[56] References Cited

U.S. PATENT DOCUMENTS 3,642,785 2/1972 Shen et al. ................ 564/219

OTHER PUBLICATIONS

Index Chemicus, 26, No. 84906, (1967).

Primary Examiner—Ethel G. Love
Attorney, Agent, or Firm—Martin L. Katz; Dennis K. Shelton; Steven F. Weinstock

[57] ABSTRACT

Disclosed herein are 1-aminoalkyl-3,4-dihydronaphthalenes represented by the formula

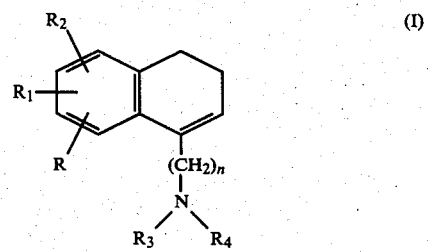

wherein n is 1 or 2; R, $R_1$, and $R_2$ are independently selected from hydrogen, hydroxy, loweralkoxy of 1 to 3 carbon atoms, loweralkenyloxy of 1 to 3 carbon atoms, thiomethyl, halo, or

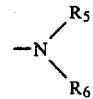

wherein $R_5$ and $R_6$ are independently selected from hydrogen, loweracyl of 1 to 4 carbon atoms or sulfonyl of the formula

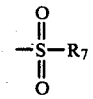

wherein $R_7$ is loweralkyl of 1 to 4 carbon atoms; or R and $R_1$, or $R_1$ and $R_2$ can be taken together to form a methylenedioxy or ethylenedioxy bridge; with the proviso that at least one of R, $R_1$ or $R_2$ must be other than hydrogen; and $R_3$ and $R_4$ are independently selected from hydrogen; loweralkyl of 1 to 4 carbon atoms; halo-substituted loweralkyl of 1 to 4 carbon atoms; arylalkyl of the formula

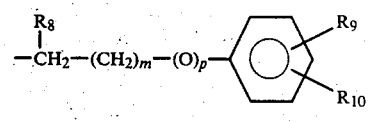

wherein m is 0, 1 or 2, p is 0 or 1, $R_8$ is hydrogen or loweralkyl of 1 to 4 carbon atoms and $R_9$ and $R_{10}$ are independently selected from hydrogen, hydroxy, methoxy, loweralkyl of 1 to 4 carbon atoms, or halo, or $R_9$ and $R_{10}$ can be taken together to form a methylenedioxy or ethylenedioxy bridge; or 1,4-benzodioxan of the formula

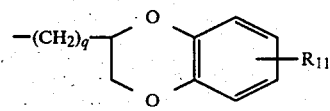

wherein q is 1, 2 or 3, and $R_{11}$ is hydrogen, methoxy, or halo; or $R_3$ and $R_4$ can be taken together to form a piperazino, piperidino or morpholino moiety; and the pharmaceutically acceptable salts thereof. Also disclosed are novel intermediates useful in the preparation of these compounds.

9 Claims, No Drawings

AMINOALKYL DIHYDRONAPHTHALENES

BACKGROUND AND SUMMARY OF THE INVENTION

This invention relates to novel aminoalkyl dihydronaphthalenes, and more particularly to 1-aminoalkyl-3,4-dihydronaphthalenes useful in the treatment of hypertension.

The adrenergic nervous system plays a major role in the innervation of heart, blood vessel and smooth muscle tissue. Agents capable of interacting with receptor sites within the adrenergic nervous system can result in a variety of physiological responses, including vasoconstriction, vasodilation, and increased or decreased heart rate (chronotropic), contractility (inotropic) and metabolic activity. In the past, various adrenergic agents have been employed to affect these and other physiological responses. However, it is highly desirable to obtain new adrenergic agents which demonstrate a high degree of specificty for differing receptor types within the adrenergic nervous system in order to obtain a desired physiological response separate from other possible, and perhaps less desirable, responses of the system. This property has been lacking from most previously employed adrenergic agents. Thus, the search continues for new and improved adrenergic agents capable of selective interaction with adrenergic receptor sites.

It has now been determined that a new class of compounds, the 1-aminoalkyl-3,4-dihydronaphthalenes, as herein defined, demonstrate an ability to interact specifically with various adrenergic receptor types and are useful as therapeutic agents in the treatment of hypertension.

DESCRIPTION OF ILLUSTRATIVE EMBODIMENTS

The present invention provides 1-aminoalkyl-3,4-dihydronaphthalenes represented by the formula I:

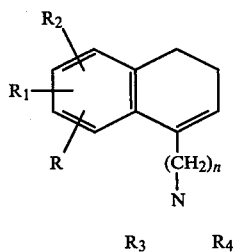

(I)

wherein n is 1 or 2; R, $R_1$, and $R_2$ are independently selected from hydrogen, hydroxy, loweralkoxy of 1–3 carbon atoms, loweralkenyloxy of 1–3 carbon atoms, thiomethyl, halo, or

wherein $R_5$ and $R_6$ are independently selected from hydrogen, loweracyl of 1 to 4 carbon atoms or sulfonyl of the formula

wherein $R_7$ is loweralkyl of 1 to 4 carbon atoms; or R and $R_1$, or $R_1$ and $R_2$ can be taken together to form a methylenedioxy or ethylenedioxy bridge; with the proviso that at least one of R, $R_1$ or $R_2$ must be other than hydrogen; and $R_3$ and $R_4$ are independently selected from hydrogen; loweralkyl of 1 to 4 carbon atoms; halo-substituted loweralkyl of 1 to 4 carbon atoms; arylalkyl of the formula

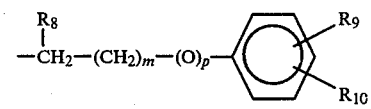

wherein m is 0, 1 or 2, p is 0 or 1, $R_8$ is hydrogen or loweralkyl of 1 to 4 carbon atoms and $R_9$ and $R_{10}$ are independently selected from hydrogen, hydroxy, methoxy, loweralkyl of 1 to 4 carbon atoms, or halo, or $R_9$ and $R_{10}$ can be taken together to form a methylenedioxy or ethylenedioxy bridge; or 1,4-benzodioxan of the formula

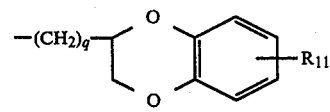

wherein q is 1, 2 or 3, and $R_{11}$ is hydrogen, methoxy, or halo; or $R_3$ and $R_4$ can be taken together to form a piperazino, piperidino or morpholino moiety, and the pharmaceutically acceptable salts thereof.

As used herein, the term "loweralkyl of 1 to 4 carbon atoms" means straight or branched chain saturated hydrocarbon radicals, such as methyl, ethyl, n-propyl, iso-propyl, n-butyl, s-butyl, and t-butyl. The term additionally includes halo-substituted loweralkyl groups such as, for example, trifluoromethyl, 2-trichloroethyl, and the like.

As used herein, the term "halo" means chloro, bromo, fluoro and iodo.

As used herein, the term "loweracyl" means an acyl group represented by the formula

wherein $R_{12}$ is loweralkyl as herein defined. Illustrative acyl groups useful in the practice of the invention are acetyl, n-propionyl, iso-propionyl, n-butyryl, s-butyryl, t-butyryl, and the like.

The term "pharmaceutically acceptable salts" refers to the pharmaceutically acceptable, relatively nontoxic, inorganic or organic acid addition salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salt of this invention can be per-N-salts.

Novel intermediates useful in the preparation of the compounds of formula I can be represented by the following formula II:

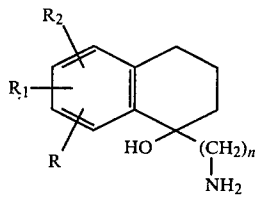

wherein n, R, $R_1$ and $R_2$ are as defined above in connection with formula I. These novel intermediate compounds are obtained from the following general reaction scheme for producing the compounds of formula (I) from suitably substituted 1,2,3,4-tetrahydro-1-naphthalenones (III) which are known in the art:

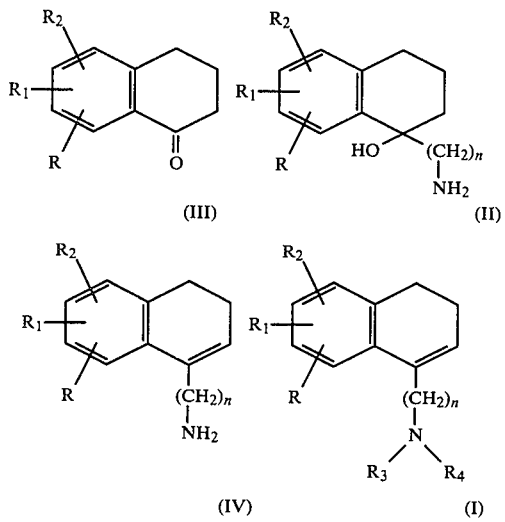

As set forth in the foregoing reaction scheme, the 1-aminoalkyl-3,4-dihydronaphthalene compounds of the invention wherein n is 1 are obtained by reacting a 1,2,3,4-tetrahydro-1-naphthalenone with, for example, trimethylsilylcyanide in the presence of a catalytic amount of, for example, aluminum trichloride followed by reduction with lithium aluminum hydride to obtain the corresponding 1-aminomethyl-1-hydroxy-1,2,3,4-tetrahydronaphthalene. Similarly, the compounds of the invention wherein n is 2 may be obtained by reacting a 1,2,3,4-tetrahydro-1-naphthalenone with, for example, acetonitrile and n-butyl lithium, followed by reduction with lithium aluminum hydride to obtain the corresponding 1-aminoethyl-1-hydroxy-1,2,3,4-tetrahydronaphthalene. The 1-aminoalkyl-1-hydroxy-1,2,3,4-tetrahydronaphthalene intermediate is then subjected to acid dehydration to obtain the corresponding 1-aminoalkyl-3,4-dihydronaphthalene compound.

The N-alkylated compounds of the invention are obtained by reacting a 1-aminoalkyl compound (IV) with an aldehyde or ketone in the presence of sodium cyanoborohydride. For example, a 1-aminoalkyl-3,4-dihydronaphthalene is reacted with formaldehyde to obtain a 1-(N,N-dimethyl)aminoalkyl-3,4-dihydronaphthalene; with acetaldehyde to obtain a 1-(N-ethyl)aminoalkyl-3,4-dihydronaphthalene; with acetone to obtain a 1-(N-isopropyl)aminoalkyl-3,4-dihydronaphthalene; etc. The N-arylalkyl compounds of the invention may be obtained by reacting the 1-aminoalkyl-3,4-dihydronaphthalene compounds (IV) with an acid halide containing the desired arylalkyl group, and then reducing the resulting amide. The N-benzodioxan compounds of the invention may be obtained by reacting a 1-aminoalkyl-3,4-dihydronaphthalene compound with 2-hydroxymethyl-1,4-benzodioxane-p-toluene sulfonate.

In addition to the foregoing, the compounds of the invention wherein R, $R_1$, and/or $R_2$ are methoxy or ethoxy may be dealkylated, such as by reaction with boron tribromide in methylene dichloride to obtain the corresponding hydroxy compound.

The foregoing may be better understood in connection with the following examples:

EXAMPLE 1

1-Aminomethyl-6,7-dimethoxy-1-hydroxy-1,2,3,4-tetrahydronaphthalene

To 20 g. of 6,7-dimethoxy-1,2,3,4-tetrahydro-1-naphthylenone is added 11.5 g. of trimethylsilylcyanide, 20 mg. of $AlCl_3$ and 16 ml. of benzene. The resulting mixture is heated and stirred at 60° until the infrared spectrum shows the absence of a carbonyl bond (about 5 hours). The resulting solution is then added dropwise to 8.4 g. of lithium aluminum hydride in 250 ml. of ether. After refluxing for 2 hours, 10 ml. of 15% NaOH is added dropwise, followed by 15 ml. of water. The mixture is stirred for 20 minutes, chloroform is added to the mixture, and then the solids are removed by filtration. The resulting organic phase is concentrated and ether is added to yield 20.3 g. (87% of theoretical yield) of 1-aminomethyl-6,7-dimethoxy-1-hydroxy-1,2,3,4-tetrahydronaphthalene; m.p. 107°–109° C.

EXAMPLE 2

1-Aminomethyl-5,6-dimethoxy-1-hydroxy-1,2,3,4-tetrahydronaphthalene 20 g. of 5,6-dimethoxy-1,2,3,4-tetrahydro1-naphthalenone is treated with trimethylsilylcyanide as described in Example 1 to yield 21.5 g. (93% of theoretical yield) of 1-aminomethyl-5,6-dimethoxy-1hydroxy-1,2,3,4-tetrahydronaphthalene; m.p. 138°–140° C.

EXAMPLE 3

1-Aminomethyl-5,6-dimethoxy-3,4-dihydronaphthalene HCl 2.50 g. of 1-aminomethyl-5,6-dimethoxy-1-hydroxy-1,2,3,4-tetrahydronaphthalene is refluxed for 90 minutes in 30 ml. of ethanol containing 3.5 ml. of saturated HCl in isopropyl alcohol. The resulting solution is concentrated and isopropyl alcohol is added to yield 2.309 g. (85% of theoretical yield) of 1-aminomethyl-5,6-dimethoxy-3,4-dihydronaphthalene HCl; m.p. 180°–182° C.

EXAMPLE 4

1-Aminomethyl-5,6-dihydroxy-3,4-dihydronaphthalene HBr

To 1.69 g. of 1-aminomethyl-5,6-dimethoxy-3,4-dihydronaphthalene HCl suspended in 25 ml. of $CH_2Cl_2$ is added dropwise 9.00 g. of BBr$_3$, while the mixture is cooled in a dry ice-acetone bath. The mixture is warmed to 0° C. and stirred for 2½ hours. The mixture is then again cooled in a dry ice-acetone bath and 50 ml. of methanol is added dropwise to the solution. The solution is then warmed to room temperature and concentrated under vacuum. Methanol is added and the solution is reconcentrated. The residue is crystallized from isopropyl alcohol and ether to yield 1.0898 g. (59% of theoretical yield) of 1-aminomethyl-5,6-dihydroxy-3,4-dihydronaphthalene HBr; m.p. 172° C.

EXAMPLE 4a

1-Aminomethyl-5,6-dimethoxy-1-hydroxy-1,2,3,4-tetrahydronaphthalene is treated with BBr$_3$ according to the method of Example 4 to obtain 1-aminomethyl-5,6-dihydroxy-3,4-dihydronaphthalene HBr identical to that obtained in Example 4.

EXAMPLE 5

1-Isopropylaminomethyl-5,6-dimethoxy-3,4-dihydronaphthalene HCl 3.00 g. of 1-aminomethyl-5,6-dimethoxy-3,4-dihydronaphthalene HCl is dissolved in 30 ml. of methanol and 30 ml. of acetone. The mixture is cooled in a nitrogen atmosphere and 1.50 g. NaBH$_3$CN is added. The resulting mixture is stirred at room temperature for 17 hours. The mixture is then cooled and 10% HCl in water is added until the solution becomes acidic. The solution is then concentrated under vacuum, made basic with KOH, and extracted with ether. The ether is dried under NaSO$_4$ and concentrated. The residue is converted to the hydrochloride salt with HCl in isopropyl alcohol to yield 2.908 g. (82% of theoretical yield) of 1-isopropylaminomethyl-5,6-dimethoxy-3,4-dihydronaphthalene HCl; m.p. 191°–194° C.

EXAMPLE 6

1-Isopropylaminomethyl-5,6-dihydroxy-3,4-dihydronaphthalene HBr 1.941 g. of 1-isopropylaminomethyl-5,6-dimethoxy-3,4-dihydronaphthalene HCl is demethylated with 10 g. of BBr$_3$ as described in Example 4 to yield 1.987 g. (95% of theoretical yield) of 1-isopropylaminomethyl-5,6-dihydroxy-3,4-dihydronaphthalene HBr; m.p. 237°–239° C.

EXAMPLE 7

1-Aminomethyl-6,7-dimethoxy-3,4-dihydronaphthalene HCl 10 g. of 1-aminomethyl-6,7-dimethoxy-1-hydroxy-1,2,3,4-tetrahydronaphthalene is treated with HCl as described in Example 3 to yield 1-aminomethyl-6,7-dimethoxy-3,4-dihydronaphthalene HCl; m.p. 197°–199° C.

EXAMPLE 8

1-aminomethyl-6,7-dihydroxy-3,4-dihydronaphthalene HBr 1.6 g. of 1-aminomethyl-6,7-dimethoxy-3,4-dihydronaphthalene HCl is demethylated with BBr$_3$ as described in Example 4 to yield 1.08 g. of 1-aminomethyl-6,7-dihydroxy-3,4-dihydronaphthalene HBr; m.p. 207°–209° C.

EXAMPLE 9

1-Aminomethyl-5,6-methylenedioxy-1-hydroxy-1,2,3,4-tetrahydronaphthalene 10 g. of 5,6-methylenedioxy-1,2,3,4tetrahydro-1-naphthalenone is reacted with 7.6 g. of trimethylsilylcyanide and the product is reduced with 6.2 g. of lithium aluminum hydride as described in Example 1 to yield 8.63 g. (74% of theoretical yield) of 1-aminomethyl-5,6-methylenedioxy-1-hydroxy-1,2,3,4-tetrahydronaphthalene; m.p. 140°–142° C.

EXAMPLE 10

1-Aminomethyl-5,6-methylenedioxy-3,4-dihydronaphthalene HCl 2.50 g. of 1-aminomethyl-5,6-methylenedioxy-1-hydroxy-1,2,3,4-tetrahydronaphthalene is refluxed with HCl in ethanol as described in Example 3 to yield 2.24 g. (83% of theoretical yield) of 1-aminomethyl-5,6-methylenedioxy-3,4-dihydronaphthalene HCl; m.p. 216°–217° C.

EXAMPLE 11

1-Dimethylaminomethyl-5,6-dihydroxy-3,4-dihydronaphthalene HBr

To 2.50 g. of 1-aminomethyl-5,6-dimethoxy-3,4-dihydronaphthalene HCl, and 12.5 ml. of 37% aqueous formalin and 25 ml. of methanol is added 1.8 g. of NaCNBH$_3$. After 1.5 hours at 45° C. the mixture is acidified with HCl and the solvents evaporated. The residue is made basic with KOH and extracted with CH$_2$Cl$_2$ to yield an oil. The oil is treated with 1.56 ml. of BBr$_3$ and 30 ml. of CH$_2$Cl$_2$ as described in Example 4 to yield 0.6 g. of 1-dimethylaminomethyl-5,6-dihydroxy-3,4-dihydronaphthalene HBr; m.p. 200°–201° C.

EXAMPLE 12

1-Aminomethyl-5-methoxy-3,4-dihydronaphthalene HCl 36.7 g. of 5-methoxy-1,2,3,4-tetrahydro-1-naphthalenone is reacted with trimethylsilylcyanide and then with lithium aluminum hydride as described in Example 1 to give 23.3 g. of 1-aminomethyl-1-hydroxy-5-methoxy-1,2,3,4-tetrahydronaphthalene. 7.3 g. of this compound is treated with HCl as described in Example 3 to yield 3.4 g. of 1-aminomethyl-5-methoxy-3,4-dihydronaphthalene HCl; m.p. 200°–202° C.

EXAMPLE 13

1-Aminomethyl-5-hydroxy-3,4-dihydronaphthalene HBr 1.5 g. of 1-aminomethyl-5-methoxy-3,4-dihydronaphthalene HCl is demethylated with BBr$_3$ as described in Example 4 to yield 1.3 g. of 1-aminomethyl-5-hydroxy-3,4-dihydronaphthalene HBr; m.p. 172°–176° C.

EXAMPLE 14

1-Aminomethyl-6-methoxy-3,4-dihydronaphthalene HCl 20 g. of 6-methoxy-1,2,3,4-tetrahydro-1-naphthalenone is reacted with trimethylsilylcyanide and then with lithium aluminum hydride as described in Example 1 to give 10.6 g. of 1-aminomethyl-1-hydroxy-6-methoxy-1,2,3,4-tetrahydronaphthalene. A sample (1.5 g.) of this compound is treated with HCl as described in Example 3 to yield 0.97 g. of 1-aminomethyl-6-methoxy-3,4-dihydronaphthalene HCl; m.p. 164°–166° C.

EXAMPLE 15

1-Aminomethyl-6-hydroxy-3,4-dihydronaphthalene HBr 1.5 g. of 1-aminomethyl-1-hydroxy-6-methoxy-1,2,3,4-tetrahydronaphthalene is demethylated and dehydrated by reacting with 1.2 ml. of $BBr_3$ and 10 ml. of $CH_2Cl_2$ as described in Example 4a to yield 1.1 g. of 1-aminomethyl-6-hydroxy-3,4-dihydronaphthalene HBr; m.p. 155°–157° C.

EXAMPLE 16

1-Aminomethyl-7-methoxy-3,4-dihydronaphthalene HCl 25 g. of 7-methoxy-1,2,3,4-tetrahydro-1-naphthalenone is reacted with trimethylsilylcyanide and then with lithium aluminum hydride as described in Example 1 to yield 28 g. of 1-aminomethyl-1-hydroxy-7-methoxy-1,2,3,4-tetrahydronaphthalene. This compound is treated with HCl in ethanol as described in Example 3 to give 1-aminomethyl-7-methoxy-3,4-dihydronaphthalene HCl; m.p. 174°–175° C.

EXAMPLE 17

1-Aminomethyl-7-hydroxy-3,4-dihydronaphthalene HBr 2.27 g. of 1-aminomethyl-7-methoxy-3,4-dihydronaphthalene HCl is demethylated with 6.26 g. of $BBr_3$ and 10 ml. of $CH_2Cl_2$ as described in Example 4 to give 1.8 g. of 1-aminomethyl-7-hydroxy-3,4-dihydronaphthalene HBr; m.p. 168°–169° C.

EXAMPLE 18

1-Aminomethyl-5-allyloxy-3,4-dihydronaphthalene HCl 5 g. of 5-allyloxy-1,2,3,4-tetrahydro-1-naphthalenone is reacted with trimethylsilylcyanide and then with lithium aluminum hydride as described in Example 1 to give 1-aminomethyl-1-hydroxy-5-allyloxy-1,2,3,4-tetrahydronaphthalene. The latter compound is treated with HCl in ethanol as described in Example 3 to give 1-aminomethyl-5-allyloxy-3,4-dihydronaphthalene HCl; m.p. 166°–167° C.

EXAMPLE 19

1-Aminomethyl-6-allyloxy-3,4-dihydronaphthalene HCl

The procedure of Example 18 is repeated using 6-allyloxy-1,2,3,4-tetrahydro-1-naphthalenone as the starting material to yield 1-aminomethyl-6-allyloxy-3,4-dihydronaphthalene HCl; m.p. 152°–153° C.

EXAMPLE 20

1-Aminomethyl-6,7-methylenedioxy-3,4-dihydronaphthalene HCl 2.4 g. of 6,7-methylenedioxy-1,2,3,4-tetrahydro-1-naphthalenone is reacted with 2.5 g. of trimethylsilylcyanide and then with lithium aluminum hydride as described in Example 1 to give 2.32 g. of 1-aminomethyl-1-hydroxy-6,7-methylenedioxy-1,2,3,4-tetrahydronaphthalene. A sample (690 mg.) of the latter compound is heated with HCl in methanol for 5 hours to yield 300 mg. of 1-aminomethyl-6,7-methylenedioxy-3,4-dihydronaphthalene HCl; m.p. 200°–201° C.

EXAMPLE 21

1-[4(4-Methoxyphenyl)-2-butylaminomethyl]-5,6-dimethoxy-3,4-dihydronaphthalene HCl 1.20 g. of 1-aminomethyl-5,6-dimethoxy-3,4-dihydronaphthalene HCl is stirred with 2.3 g. of 4(4-methoxyphenyl)-2-butanone and 560 mg. of $NaCNBH_3$ in 20 ml. of methanol for 6 hours at room temperature. The reaction mixture is cooled and 10% HCl is added until the solution becomes acidic. The solution is then concentrated under vacuum and made basic with KOH. The solution is then extracted with ether, dried over $Na_2SO_4$ and concentrated. The residue is converted to the hydrochloride salt with HCl and isopropyl alcohol to yield 1.28 g. of 1-[4(4-methoxyphenyl)-2-butylaminomethyl]-5,6-dimethoxy-3,4-dihydronaphthalene HCl; m.p. 171°–174° C.

EXAMPLE 22

1-Aminomethyl-5,6-dichloro-3,4-dihydronaphthalene HCl 1.5 g. of 5,6-dichloro-1,2,3,4-tetrahydro-1-naphthalenone is reacted with 2.08 g. of trimethylsilylcyanide and then with lithium aluminum hydride as described in Example 1 to give 1.4 g. of 1-aminoethyl-1-hydroxy-1,2,3,4-tetrahydro-5,6-dichloronaphthalene. The latter compound is refluxed for 20 hours with 40 ml. of a saturated solution of HCl gas in isopropyl alcohol. The solvent is evaporated to yield 1.04 g. of 1-aminomethyl-5,6-dichloro-3,4-dihydronaphthalene HCl; m.p. 224°–226° C.

EXAMPLE 23

1-Aminomethyl-6,7-dichloro-3,4-dihydronaphthalene HCl 2.0 g. of 6,7-dichloro-1,2,3,4-tetrahydro-1-naphthalenone is treated with trimethylsilylcyanide and then with lithium aluminum hydride and HCl as described in Example 22 to yield 1.10 g. of 1-aminomethyl-6,7-dichloro-3,4-dihydronaphthalene HCl; m.p. >280° C.

EXAMPLE 24

1-Isopropylaminomethyl-6,7-dichloro-3,4-dihydronaphthalene HCl 500 mg. of 1-aminomethyl-6,7-dichloro-3,4-dihydronaphthalene HCl is reacted with 5 ml. of acetone, 250 mg. of $NaCNBH_3$ in 10 ml. of methanol according to the method of Example 5 to yield 363 mg. of 1-isopropylaminomethyl-6,7-dichloro-3,4-dihydronaphthalene HCl; m.p. 190°–192° C.

EXAMPLE 25

1-Isopropylaminomethyl-5,6-dichloro-3,4-dihydronaphthalene HCl 1.00 g. of 1-aminomethyl-5,6-dichloro-3,4-dihydronaphthalene HCl is reacted with 20 ml. of acetone and 500 mg. of $NaCNBH_3$ in 10 ml. of methanol by the method of Example 5 to yield 0.8 g. of 1-isopropylaminomethyl-5,6-dichloro-3,4-dihydronaphthalene HCl; m.p. 255°–258° C.

EXAMPLE 26

1-Aminomethyl-5-fluoro-3,4-dihydronaphthalene HCl

5-Fluoro-1,2,3,4-tetrahydro-1-naphthalenone is treated according to the method of Example 22 to obtain 5-aminomethyl-5-fluoro-3,4-dihydronaphthalene HCl; m.p. 215°–218° C.

EXAMPLE 27

1-Aminomethyl-5-chloro-3,4-dihydronaphthalene HCl

5-Chloro-1,2,3,4-tetrahydro-1-naphthalenone is treated according to the method of Example 22 to obtain 1-aminomethyl-5-chloro-3,4-dihydronaphthalene HCl; m.p. 217°–219° C.

EXAMPLE 28

1-Aminomethyl-6-fluoro-3,4-dihydronaphthalene HCl

6-Fluoro-1,2,3,4-tetrahydro-1-naphthalenone is treated according to the method of Example 22 to obtain 1-aminomethyl-6-fluoro-3,4-dihydronaphthalene HCl; m.p. 230°–233° C.

EXAMPLE 29

1-Aminomethyl-6-chloro-3,4-dihydronaphthalene HCl

6-Chloro-1,2,3,4-tetrahydro-1-naphthalenone is treated according to the method of Example 22 to obtain 1-aminomethyl-6-chloro-3,4-dihydronaphthalene HCl; m.p. 206°–208° C.

EXAMPLE 30

1-[3(4-Methoxyphenyl)propylaminomethyl]-3,4-dihydronaphthalene HCl 1.80 g. of 3(4-methoxyphenyl)propionic acid is converted to the acid chloride by refluxing with 1.47 ml. of PCl$_3$ and 23 ml. of benzene. The acid chloride is added dropwise to 1.76 g. of 1-aminomethyl-1-hydroxy-1,2,3,4-tetrahydronaphthalene and 3.2 ml. of triethylamine in methylene chloride. The mixture is stirred and then extracted, first with 1 N HCl and then with 10% NaOH. The solution is dried over MgSO$_4$ and the solvents are removed to give the intermediate hydroxy amide. The latter intermediate compound is refluxed with 27 ml. of 1 molar BH$_3$ in tetrahydrofuran (THF) for 3 hours. To this solution is added 8 ml. of concentrated HCl and the solvents are concentrated at atmospheric pressure. The concentrated solution is extracted with CH$_2$Cl$_2$ and NaOH, the organic layer is separated and concentrated, then acidified with HCl to yield 1-[3(4-methoxyphenyl)propylaminomethyl]-3,4-dihydronaphthalene HCl; m.p. 79° C.

EXAMPLE 31

1-(2-Aminoethyl)-6,7-dichloro-3,4-dihydronaphthalene HCl

To 11.9 ml. of 1.55 M n-butyl lithium in hexane and 20 ml. of THF at −78° C. is added 1.1 ml. of acetonitrile in 10 ml. of THF. The mixture is stirred at −78° C. for 1 hour. To this reaction mixture is added 3.00 g. of 6,7-dichloro-1,2,3,4-tetrahydro-1-naphthalenone in 60 ml. of THF. The reaction mixture is warmed to room temperature and 1.30 g. of lithium aluminum hydride is added. The mixture is stirred at room temperature for 3 hours and the lithium aluminum hydride is decomposed with H$_2$O and 50% NaOH. The solids are removed and the solution is concentrated. The residue is refluxed for 17 hours with 30 ml. of isopropyl alcohol saturated with HCl. The solution is then concentrated to yield 910 mg. of 1-(2-aminoethyl)-6,7-dichloro-3,4-dihydronaphthalene HCl; m.p. 190°–210° C.

EXAMPLE 32

1-Aminomethyl-3,4-dihydro-6-benzyloxy-5-(N-benzyl-N-methanesulfonylamino)naphthalene HCl 6-benzyl-5-(N-benzyl-N-methanesulfonylamino)-1,2,3,4-tetrahydro-1-naphthalenone (Chem. Pharm. Bull. 25, 3289, 1977) is reacted with trimethylsilylcyanide and lithium aluminum hydride as described in Example 1 to give the intermediate aminohydroxy compound. The latter intermediate is refluxed in ethanol with HCl to yield 1-aminomethyl-3,4-dihydro-6-benzyloxy-5-(N-benzyl-N-methanesulfonylamino)naphthalene HCl; m.p. 214°–215° C.

EXAMPLE 33

1-Aminomethyl-3,4-dihydro-6-hydroxy-5-methanesulfonylamino naphthalene HBr

The dibenzyl compound of Example 32 is treated with BBr$_3$ in CH$_2$Cl$_2$ to yield 1-aminomethyl-3,4-dihydro-6-hydroxy-5-methanesulfonylamino naphthalene HBr.

EXAMPLE 34

1-Aminomethyl-5-chloro-6-methoxy-3,4-dihydronaphthalene HCl 5-chloro-6-methoxy-1,2,3,4-tetrahydro-1-naphthalenone (m.p. 130°–131° C.) is prepared from 5-amino-6-methoxy-1,2,3,4-tetrahydro-1-naphthalenone by the Sandmeyer reaction. This ketone is reacted with trimethylsilylcyanide followed by lithium aluminum hydride according to the method of Example 1 to obtain the intermediate 1-aminomethyl-1-hydroxy-5-chloro-6-methoxy-1,2,3,4-tetrahydronaphthalene. The latter intermediate compound is refluxed in HCl to yield 1-aminomethyl-5-chloro-6-methoxy-3,4-dihydronaphthalene HCl; m.p. 221°–222° C.

EXAMPLE 35

5-Methylthio-8-methoxy-1,2,3,4-tetrahydro-1-naphthalenone

4(3-methoxyphenyl)butyric acid ethyl ester is iodinated with iodine and silver trifluoroacetate in methylene chloride to give 4(6-iodo-3-methoxyphenyl)butyric acid ethyl ester. This compound is heated at 80° C. with methylthiolithium in dimethylformamide in the presence of CuO. The resulting product is hydrolyzed with NaOH to give 4(6-methylthio-3-methoxyphenyl)butyric acid, which is cyclyzed with polyphosphoric acid to obtain 5-methylthio-8-methoxy-1,2,3,4-tetrahydro-1-naphthalenone.

EXAMPLE 36

1-Aminomethyl-5-methylthio-8-methoxy-3,4-dihydronaphthalene HCl 5-methylthio-8-methoxy-1,2,3,4-tetrahydro-1-naphthalenone is reacted with trimethylsilylcyanide followed by lithium aluminum hydride, and the resulting intermediate hydroxy amino compound is dehydrated with HCl, according to the procedure of Examples 1 and 3, to yield 1-aminomethyl-5-methylthio-8-methoxy-3,4-dihydronaphthalene HCl.

EXAMPLE 37

1-(2-(1,4-Benzodioxan)-methylaminomethyl)-5,6-methylenedioxy-3,4-dihydronaphthalene HCl 1-aminomethyl-5,6-methylenedioxy-3,4-dihydronaphthalene HCl is neutralized to obtain the free base, and then heated overnight with 2-hydroxymethyl-1,4-benzodioxan-p-toluenesulfonate and diisopropylethylamine to obtain 1-(2-(1,4-benzodioxan)-methylaminomethyl)-5,6-methylenedioxy-3,4-dihydronaphthalene HCl.

EXAMPLE 38

1-[2(4-Chloro-2,6-dimethoxyphenoxy)-ethylaminomethyl]-5,6-dimethoxy-3,4-dihydronaphthalene HCl 1-aminomethyl-5,6-dimethoxy-1-hydroxy-1,2,3,4-tetrahydronaphthalene is reacted with the acid chloride of 4-chloro-2,6-dimethoxyphenoxy acetic acid. The resulting amide is reduced with diborane and dehydrated with HCl as described in Example 30 to obtain 1-[2(4-chloro-2,6-dimethoxyphenoxy)ethylaminomethyl]-5,6dimethoxy-3,4-dihydronaphthalene HCl.

EXAMPLE 39

1-Aminomethyl-6-amino-5,7-dichloro-3,4-dihydronaphthalene HCl 6-amino-1,2,3,4-tetrahydro-1-naphthalenone is reacted with trimethylsilylcyanide followed by lithium aluminum hydride to obtain 1-aminomethyl-1-hydroxy-6-amino-1,2,3,4-tetrahydronaphthalene. This diamine is di-acetylated with acetic anhydride, chlorinated with chlorine and acetic acid, and then heated to dehydrate the alcohol. The resulting di-chloro-di-acetamide is hydrolyzed in HCl to obtain 1-aminomethyl-6-amino-5,7-dichloro-3,4-dihydronaphthalene HCl.

EXAMPLE 40

1-Aminomethyl-5-formamido-6-benzyloxy-3,4-dihydronaphthalene HCl 5-amino-6-benzyloxy-1,2,3,4-tetrahydro-1-naphthalenone (such as that disclosed in U.S. Pat. No. 4,035,512) is reacted with trimethylsilylcyanide followed by lithium aluminum hydride. The resultant 1-hydroxy-1-aminomethyl compound is dehydrated with HCl to give 1-aminomethyl-5-amino-6-benzyloxy-3,4-dihydronaphthalene HCl. This latter compound is reacted with trifluoro acetic anhydride to give 1-trifluoroacetylaminomethyl-5-amino-6-benzyloxy-3,4-dihydronaphthalene. This latter compound is formylated with formic acid and acetic anhydride and the trifluoroacetyl group is removed with $Na_2CO_3$ to yield 1-aminomethyl-5-formamido 6-benzyloxy-3,4-dihydronaphthalene HCl.

EXAMPLE 41

1-(2[4-(2-Methoxyphenyl)piperazinyl]ethyl)-5,6-dimethoxy-3,4-dihydronaphthalene HCl tert-Butylacetate is added to a solution of lithium di-isopropyl amide in THF at −78° C. To this solution is added 5,6-dimethoxy-1,2,3,4-tetrahydro-1-naphthalenone and the resulting mixture is stirred at 0° C. for 20 minutes, then cooled back to −78° C. One equivalent of HCl in water is added to the solution, followed by concentration of this mixture. The residue is heated with a solution of HCl/acetic acid (1:1) in water and methanol for 20 minutes, giving 5,6-dimethoxy-3,4-dihydronaphthalene-1-acetic acid. The latter acid is refluxed in benzene with $PCl_3$ for one hour. This solution is filtered while hot, and the filtrate is concentrated and added to at 0° C. triethylamine and 1-(2-methoxyphenyl)piperazine in chloroform to give the corresponding amide. This intermediate product is reduced to the amine by refluxing in THF with lithium aluminum hydride for 2 hours and decomposing the excess lithium aluminum hydride with $H_2O$ and NaOH. The lithium and aluminum salts are removed, the THF concentrated, and the residue treated with HCl and isopropyl alcohol to yield 1-(2[4-(2-methoxyphenyl) piperazinyl]ethyl)-5,6-dimethoxy-3,4-dihydronaphthalene HCl.

EXAMPLE 42

1-([4-(4-Fluorophenyl)-piperazinyl]-methyl)-6-chloro-3,4-dihydronaphthalene HCl 6-chloro-1,2,3,4-tetrahydro-1-naphthalenone s heated with 2 equivalents of trimethylsilylcyanide and a catalytic amount of $AlCl_3$ for 4 hours at 70° C. The resulting product is refluxed with a saturated solution of HCl in methanol for 16 hours and the solution is concentrated and treated with KOH and methanol then refluxed for an additional 1 hour. The solution is concentrated and acidified with HCl to give 1-carboxyl-6-chloro-3,4-dihydronaphthalene. The latter intermediate compound is treated with $PCl_3$ and then 1-(4-fluorophenyl)piperazine as described in Example 41. The resulting amide is reduced with lithium aluminum hydride as described in Example 41 to obtain 1-([4-(4-fluorophenyl)-piperazinyl]methyl)-6-chloro-3,4-dihydronaphthalene HCl.

EXAMPLE 43

1-(2-(1,4-benzodioxan)-methylaminomethyl)-5-allyloxy-3,4-dihydronaphthalene HCl

To a suspension of 1.5 g. of 1-aminomethyl-5-allyloxy-3,4-dihydronaphthalene HCl in 8.0 ml. of acetonitrile is added 3.0 g. of 2-hydroxymethyl-1,4-benzodioxan-p-toluenesulfonate followed by 6.8 ml. of diisopropylethylamine, and the resulting mixture is heated at reflux for 18 hours. An additional 1.0 g. of 2-hydromethyl-1,4-benzodioxan-p-toluene sulfonate is added to the mixture and heating at reflux is continued for 2 days. The reaction mixture is cooled to room temperature and evaporated. The residue is dissolved in methylene chloride, washed with 10% sodium bicarbonate, dried over magnesium sulfate, filtered and evaporated to produce an oil. The oil is dissolved in methylene chloride and a sufficient amount of ethereal HCl is added to form a solution of the hydrochloride salt. This solution is washed with 1 N- HCl, dried over magnesium sulfate, filtered and evaporated. Crystalization from acetonitrile yields 1.4 g. of 1-(2-(1,4-benzodioxan)-methylaminomethyl)-5-allyloxy3,4-dihydronaphthalene HCl; m.p. 174°–176° C.

The therapeutic activity of the compounds of formula I can be demonstrated by their ability to decrease arterial blood pressure and/or heart rate in the spontaneously hypertensive rat as follows. A group of Okamoto rats, which develop hypertension spontaneously when reaching young adulthood, are deprived of food for a period of 16 hours and are placed in semi-restraining wire mesh cylinders maintained at a constant temperature of 36° C. An occluding cuff, operatively connected to a programmed sphygmomanometer, is placed over the tail of each rat of the group and retained near the tail base. The pressure of each cuff is automatically, cyclically increased within the range of from 0 to 250 mm Hg. at the rate of 10 mm Hg./sec., the total inflation and deflation time of each cycle being 50 seconds, with a 10 second rest period between cycles. A photocell is placed distal to the cuff to detect pulses resulting from the forward motion of blood flow with each heartbeat of the rat. As the pressure in the cuff increases, measurable pulses disappear at the point where the cuff pressure equals the arterial blood pressure. Measurable pulses reappear during deflation at approximatley the same pressure, and aterial blood pressure is thereby established by cuff pressure at the point of pulse appearance. The heart rate is determined from the arterial pulse wave. A 100 mg./kg. dose of a test compound of formula I is administered orally to each rat of the test group, and five interference-free signals are recorded on a Model 7 Grass polygraph for each rat at various measurement periods following administration. By following the foregoing procedure, the test compounds are shown to decrease the arterial blood pressure and/or heart rate of rats of the group.

The compounds of the invention can be administered in any effective pharmaceutically acceptable form to warm blooded animals, e.g., in oral, parenteral or infusable dosage forms, or as a buccal or nasal spray. Suitable parenteral routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, an dispersing agents. They may be sterilized, for example, by filtration through a bacteria-retaining filter, or by incorporating sterilizing agents into the compositions. They can also be manufactured in the form of sterile solid compositions which can be dissolved in sterile water, or other sterile injectable medium, immediately before use.

Solid dosage forms for oral administration include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, dosage levels of about 0.1 to about 200, more preferably about 0.5 to about 150 and most preferably about 1 to about 125 mg. of active ingredient per kg. of body weight per day are administered orally to a mammalian patient suffering from hypertension. If desired, the daily dose may be divided into multiple doses for administration, e.g., two to four separate doses per day.

What is claimed is:

1. A compound of the formula

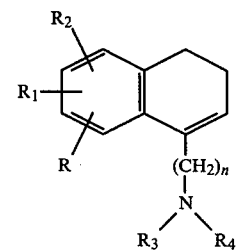

wherein n is 1 or 2; R, $R_1$, and $R_2$ are independently selected from hydrogen, hydroxy, loweralkoxy of 1 to 3 carbon atoms, loweralkenyloxy of 1 to 3 carbon atoms, thiomethyl, halo, or

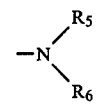

wherein $R_5$ and $R_6$ are independently selected from hydrogen, loweracyl of 1 to 4 carbon atoms or sulfonyl of the formula

wherein $R_7$ is loweralkyl of 1 to 4 carbon atoms; with the proviso that at least one of R, $R_1$ or $R_2$ must be other than hydrogen; and $R_3$ and $R_4$ are independently selected from hydrogen; loweralkyl of 1 to 4 carbon atoms; halo-substituted loweralkyl of 1 to 4 carbon atoms; arylalkyl of the formula

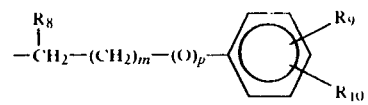

wherein m is 0, 1 or 2, p is 0 or 1, $R_8$ is hydrogen or loweralkyl of 1 to 4 carbon atoms and $R_9$ and $R_{10}$ are independently selected from hydrogen, hydroxy, methoxy, loweralkyl of 1 to 4 carbon atoms, or halo; and the pharmaceutically acceptable salts thereof.

2. A compound of claim 1 wherein one of R, $R_1$, and $R_2$ is hydrogen and the remaining two of R, $R_1$ and $R_2$ are hydroxy.

3. A compound of claim 1 wherein one of R, $R_1$ and $R_2$ is hydrogen and the remaining two of R, $R_1$ and $R_2$ are methoxy.

4. A compound of claims 1, 2, or 3 wherein $R_3$ and $R_4$ are hydrogen.

5. A compound of claims 1, 2, or 3 wherein $R_3$ is isopropyl and $R_4$ is hydrogen.

6. A compound of claims 1, 2, or 3 wherein $R_3$ is aryloxyalkyl of the formula

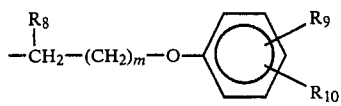

wherein m, $R_8$, $R_9$ and $R_{10}$ are as defined in claim 1, and wherein $R_4$ is hydrogen.

7. A compound of claims 1, 2, or 3 wherein $R_3$ is arylalkyl of the formula

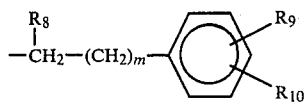

wherein m, $R_8$, $R_9$ and $R_{10}$ are as defined in claim 1, and wherein $R_4$ is hydrogen.

8. A compound of claims 1, 2, or 3 wherein $R_3$ and $R_4$ are methyl.

9. A composition for the treatment of hypertension in a pharmaceutical dosage form comprising an antihypertensive effective amount of a compound of the formula

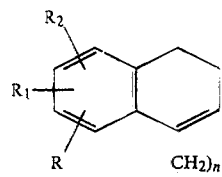

wherein n is 1 or 2; R, $R_1$, and $R_2$ are independently selected from hydrogen, hydroxy, loweralkoxy of 1 to 3 carbon atoms, loweralkenyloxy of 1 to 3 carbon atoms, thiomethyl, halo, or

wherein $R_5$ and $R_6$ are independently selected from hydrogen, loweracyl of 1 to 4 carbon atoms or sulfonyl of the formula

wherein $R_7$ is loweralkyl of 1 to 4 carbon atoms; with the proviso that at least one of R, $R_1$ or $R_2$ must be other than hydrogen; and $R_3$ and $R_4$ are independently selected from hydrogen; loweralkyl of 1 to 4 carbon atoms; halo-substituted loweralkyl of 1 to 4 carbon atoms; arylalkyl of the formula

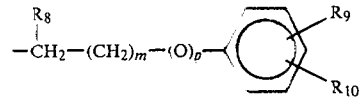

wherein m is 0, 1 or 2, p is 0 or 1, $R_8$ is hydrogen or loweralkyl of 1 to 4 carbon atoms and $R_9$ and $R_{10}$ are independently selected from hydrogen, hydroxy, methoxy, loweralkyl of 1 to 4 carbon atoms, or halo; and the pharmaceutically acceptable salts thereof and a pharmaceutically acceptable carrier or diluent.

* * * * *